United States Patent [19]

Takatori et al.

[11] Plant 4,677

[45] Mar. 24, 1981

[54] ASPARAGUS PLANT

[75] Inventors: Frank H. Takatori; Franklin D. Souther, both of Riverside, Calif.

[73] Assignee: The Regents of the University of California, Berkeley, Calif.

[21] Appl. No.: 105,431

[22] Filed: Dec. 19, 1979

[51] Int. Cl.[3] ..... A01H 5/00

[52] U.S. Cl. ..... Plt./89

[58] Field of Search ..... Plt./89

*Primary Examiner*—James R. Feyrer

*Attorney, Agent, or Firm*—Townsend and Townsend

[57] ABSTRACT

A new and distinct variety of female asparagus plant primarily characterized by its high lateral branching which initiates from the 19–22 node (about 19 inches above soil level), its vigorous growth and canes which grow to a height exceeding six feet, and further characterized by its fruit color which changes during its stages of maturing from green to orange to red.

2 Drawing Figures

DESCRIPTION

This invention relates to a new and distinct female clone of asparagus designated as F-109. Plant F-109 was selected from a plot of variety U.C. 309, which was planted at the University of California Agricultural Experiment Station, Riverside, Calif., in 1963. The source of seed for the U.C. 309 planting was obtained from Mr. J. Hanna, formerly a member of the Department of Vegetable Crops, University of California, Davis, Calif.

Female plant F-109 is a vigorous growing multi-caned plant that grows erect to a height exceeding six feet and in most production areas will be larger than plant M-120. A well established F-109 plant, three years or older in age, will produce between 15 and 20 canes per plant per year. The canes measured at soil level will range between 1 and 1¼ inches in diameter.

Plant growth is erect and the foliage referred to as fern is Dark Green (Plate XVIII) in color. The first lateral branch occurs about 19.0 inches above the soil level and exhibits a plant characteristic referred to as "high branching." This characteristic is a particularly distinguishing one from other known varieties of asparagus.

Asparagus is a dioecious plant, individual plants being either male or female in sex.

In the accompanying drawing.

Figure 1:
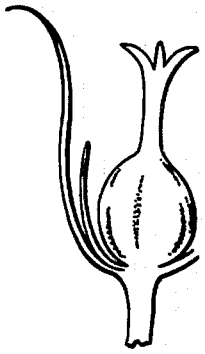
FIG. 1 shows typical female parts of F-109.
Figure 2:
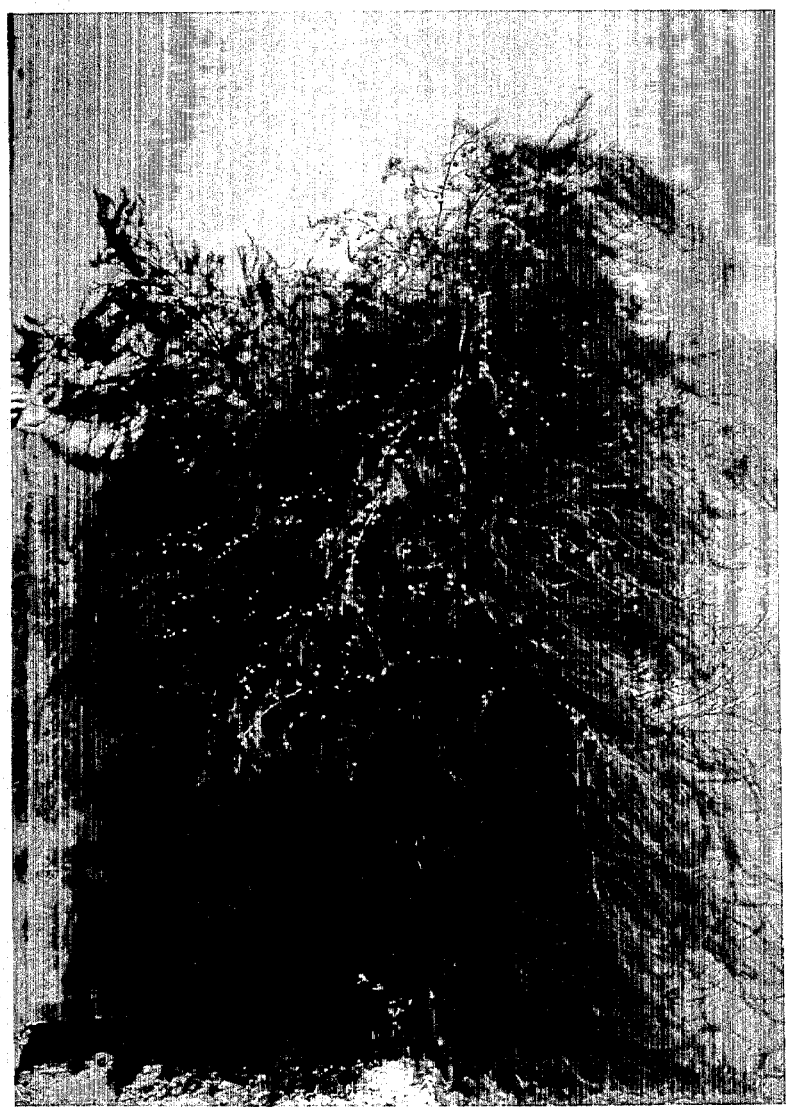
FIG. 2 shows the "high branching" characteristic of this variety and erect growth.

The only existing methods of asexual reproduction of asparagus plants for the multiplication of plants of this invention are crown division or tissue culture. The plant of this invention has been asexually reproduced by tissue culture techniques which are more conducive to large scale multiplcation of asparagus plants than is crown division.

The colors designated hereinafter are approximate and may vary with several factors including soil type, nutrition, temperature and maturity. The colors have been determined by comparison to the colors in "Color Standards and Color Nomenclature" by Robert Ridgway, Washington, D.C., 1912.

PLANT CHARACTERISTICS

Spear: Straight, smooth and round with slow taper terminating in a tight compact head. Bracts covering nodes, Lumiere Green (Plate XVII) in color, tightly adhering to the spear. Lateral branches are initiated from the 19–22 node when the spears are 13 to 15 inches in height. Spear color is Biscay Green (Plate XVII). Emergence in the spring is early. The spear bract is Lumiere Green (Plate XVII).

Foliage: An erect perennial herb Light Bice Green (Plate XVII) with smooth straight stems, referred to as "canes," with many lateral branches above the 19th node and around 19 to 20 inches above the soil level. A three year or older plant will develop between 15 and 20 canes, 1 to 1¼ inches in diameter that grow to a height in excess of six feet. The mature cane is Grass Green (Plate VI) and the cane bract is Ochraceous-Buff (Plate XV).

Asparagus does not possess true leaves. F-109 has 10.07 (avg.) cladophyll whorls/5 cm. of stem length with an average of 5.10 cladophylls/whorl. Photosynthetic "leaf area" is 7.01 mm.$^2$ per mg. dry weight.

Inflorescence: One to four, usually two in the axil with cladodes. Flowers (0.40 to 0.45 cm. length) are Pale Viridine Yellow (Plate V), campanulate, no stamens on pedicels.

Fruit: Diameter 0.8 to 0.88 cm. average diameter, with color change from Light Bice Green (Plate XVII) (immature) to Chocolate (Plate XXVIII) to Orange (Plate II), Scarlet-Red to Nopal Red (Plate I) at maturity. Seed number varies from 1 to 9 per berry.

Crown-root system: Crown a woody rhizome with long fleshy storage roots and fibrous absorptive roots originating from the fleshy storage roots. Storage roots, numerous, ¼ to ⅜ inch in diameter and extending over five feet in all directions.

We claim:

1. The new and distinct variety of asparagus plant herein described and illustrated and identified by the characteristics enumerated above.

* * * * *